(12) United States Patent
Turner et al.

(10) Patent No.: US 6,804,998 B2
(45) Date of Patent: *Oct. 19, 2004

(54) METHOD OF WEAR TESTING A TIRE

(75) Inventors: John L. Turner, Akron, OH (US); David O. Stalnaker, Hartville, OH (US)

(73) Assignee: Bridgestone/Firestone North American Tire, LLC, Nashville, TN (US)

( * ) Notice: Subject to any disclaimer, the term of this patent is extended or adjusted under 35 U.S.C. 154(b) by 199 days.

This patent is subject to a terminal disclaimer.

(21) Appl. No.: 09/976,065

(22) Filed: Oct. 12, 2001

(65) Prior Publication Data

US 2002/0124638 A1 Sep. 12, 2002

Related U.S. Application Data

(63) Continuation-in-part of application No. 09/770,884, filed on Jan. 26, 2001.

(51) Int. Cl.$^7$ ................................................ E01C 23/00
(52) U.S. Cl. ................................................ 73/146; 73/8
(58) Field of Search ................................ 73/146, 146.2, 73/146.3, 146.4, 146.5, 146.8

(56) References Cited

U.S. PATENT DOCUMENTS

3,563,088 A     2/1971   Sperberg

FOREIGN PATENT DOCUMENTS

| EP | 0 880 019 A2 | 11/1998 |
| EP | 0 969 276 A2 | 1/2000 |
| EP | 0 955 534 A3 | 3/2000 |

*Primary Examiner*—Edward Lefkowitz
*Assistant Examiner*—Andre Allen
(74) *Attorney, Agent, or Firm*—Fred H. Zollinger, III; Michael R. Huber

(57) ABSTRACT

A method for indoor wear testing tires includes the steps of characterizing a vehicle and a wear test course and combining the characterized data to create input data for an indoor wear test machine. The input data allows the indoor wear test machine to accurately simulate an outdoor wear test course for the characterized vehicle. The method allows multiple wear test courses to be used with a single characterized vehicle and allows a single wear test course to be used with multiple characterized vehicles. The method allows tires to be wear tested in relatively short time periods in the controlled environment of the indoor laboratory. In addition, the method is relatively easy to set up and perform.

16 Claims, 3 Drawing Sheets

METHOD OF WEAR TESTING A TIRE

CROSS REFERENCE TO RELATED APPLICATION

This is a continuation-in-part application claiming priority from U.S. patent application Ser. No. 09/770,884 filed Jan. 26, 2001, titled A Method of Wear Testing a Tire; the disclosures of which are incorporated herein by reference.

BACKGROUND OF THE INVENTION

1. Technical Field

The present invention generally relates to methods of wear testing tires and, more particularly, to a method for defining a tire load history that is used in an indoor wear test. Specifically, the present invention relates to a method of defining a tire load history and using the tire load history to conduct an indoor wear test on the tire.

2. Background Information

Automobile and tire manufacturers desire wear testing to be performed on tires. Different methods of wear testing tires are known in the art. In one known method, the test tires are placed on a vehicle that will be frequently driven. The tires are measured after the vehicle is driven a selected number of miles. Another known test procedure is performed indoor on a wear test drum. A wear test drum provides a rotating surface that engages the tire to simulate a road surface. The wear test drum provides mechanisms for varying the force between the tire and the rotating surface. The velocity of the rotating surface may also be varied. The user may simulate actual public road driving conditions by varying these forces and the velocity. The problem in the prior art is that the user cannot easily determine what forces and velocities to use to simulate public road driving conditions for a specific vehicle.

For instance, one may wish to simulate tire wear with a specific tire on a specific vehicle over a daily commute that includes country road, highway, and city road driving conditions. The total length of the daily commute over a one year period may be 15,000 miles. The forces between the tire and the road constantly change through this commute and the person conducting the indoor wear test desires to accurately simulate these forces on the test tire with the indoor test drum.

One method of predicting the tire forces is to instrument a test vehicle with wheel force transducers that are mounted as part of the wheel and rotate with the wheel/tire assembly while the vehicle is driven over a controlled test track. The vehicle is equipped with a data acquisition system that stores signals from the transducers. For instance, front and rear radial force, lateral force, drive/brake force, and tire velocities may be recorded. A problem with this measurement system is that the equipment is difficult to transport from test location to test location, the setup time is long, and the vehicle cannot be driven on public roads while equipped with the transducers. The data is thus only gathered on a test track that simulates public road driving conditions. The process of gathering the force histories for a given car with a given tire is expensive and often consumes weeks of time. The process must be repeated for different cars and for different tires. The art thus desires a faster and easier method of generating tire loading histories for indoor wear tests. The art also desires that the method for generating the tire loading histories result in more accurate load histories for the test machine.

SUMMARY OF THE INVENTION

The present invention provides a method for determining tire load histories for use with an indoor wear test machine. In one embodiment of the invention, sample tire forces are measured with a vehicle test system. The data from the test system is used to create formulas that relate the tire forces to the accelerations experienced by the vehicle. In another embodiment of the invention, a computer model of the vehicle may be used to conduct a set of basic maneuvers to provide the data to create the formulas that relate the tire forces to the accelerations experienced by the vehicle.

An instrumented vehicle driven over a wear test course records data which is used to generate a "signature" for that course. This data is used with the formulas to create the input forces for an indoor wear test machine. In one embodiment of the invention, the data is gathered at a fixed distance interval rather than a fixed time interval.

The invention also provides a method of translating the data gathered from the outdoor test vehicle into tire load data that may be used to operate an indoor tire wear test drum to perform an indoor tire wear test.

DETAILED DESCRIPTION OF THE DRAWINGS

The method of the present invention is generally performed by first characterizing the vehicle for which the tire is being wear tested. The method also requires a wear test course to be characterized. The invention combines a course characterization with a vehicle characterization to create a load history that is used to drive an indoor mechanical wear test machine to wear test the tire. The resulting wear test accurately reflects the wear on the tire if the tire had been used on the vehicle over the test course. In addition to the convenience and time advantages, the test courses may be used with any vehicle characterizations to allow different vehicles to be tested on a single course. In addition, different courses may be used with a single vehicle characterization to compare how a tire will perform with a vehicle on different courses. The uncontrolled effect of weather variability is also avoided.

1. Vehicle Characterization

The vehicle characterization step of this method measures the forces and inclination angles experienced by each tire of a vehicle under a variety of driving conditions. The vehicle characterization step is performed on the vehicle for which the tires are to be wear tested. For instance, if the tire to be wear tested is going to be used on a specific passenger car, the specific passenger car—or a similar car—should be used during the vehicle characterization step.

Figure 1:
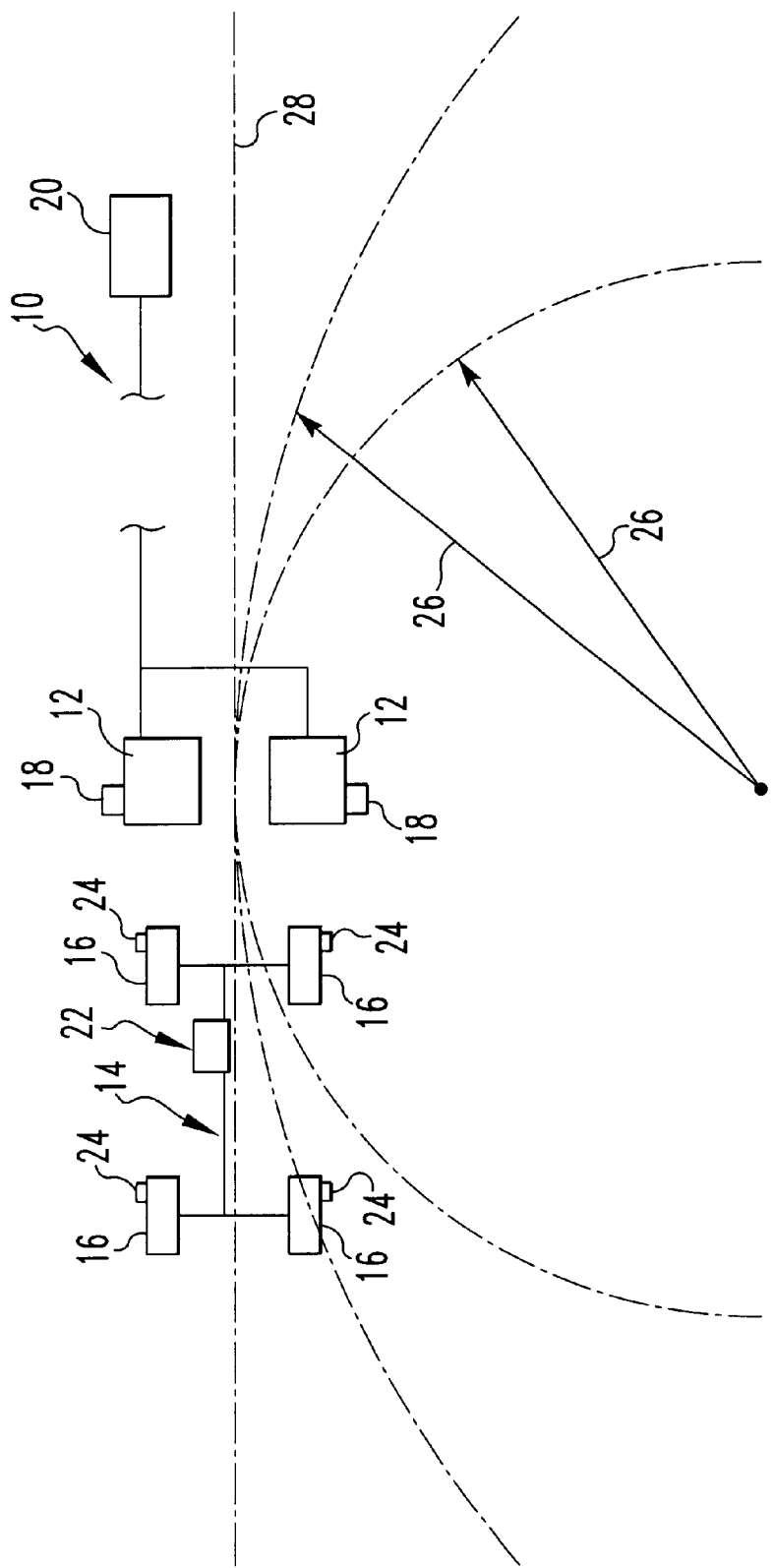
FIG. 1 is a schematic view of a dual force platform test facility.

The vehicle characterization step may be repeated for each type of vehicle for which a tire is to be wear tested. In one embodiment of the invention, the vehicle characterization data may be gathered using a dual force platform measurement system 10 (FIG. 1). One system known in the art is referred to as AMTI Model OR6-5-2000. This system includes in-ground force platforms 12 configured to be driven over by the vehicle 14. The platform spacing is adjustable to accommodate different vehicle track widths. When the tires 16 of the vehicle 14 engage the force platforms 12, three directional forces (fore-aft (Fx), lateral (Fy), and vertical (Fz)) are measured by transducers 18 and recorded by an appropriate storage device 20 such as a computer. The data may be immediately stored by computer 20 or stored in an intermediate storage device and then stored in computer 20. Transducers 18 may be in communication with storage device 20 by wires or wireless transmissions. A measurement device may be used to measure the speed of vehicle 14. In another embodiment of the invention, the vehicle speed may be processed from the data gathered as tires 16 pass over platforms 12.

In addition to the directional force measurements, transducers 22 are positioned at the vehicle center of gravity to measure accelerations (fore-aft, lateral, and vertical) during passage of tires 16 across force platforms 12. Appropriate wheel inclination measurement devices 24 are also used to measure the wheel inclination angles while tires 16 are passing over force platforms 12. One type of wheel inclination angle measurement device is disclosed in U.S. Pat. No. 5,561,244. Data from the two load platforms, the in-vehicle measurement of accelerations, and from the wheel inclination device are collected simultaneously.

The directional forces, velocity, accelerations, and wheel inclination angles are measured while vehicle 14 passes over platforms 12 at a range of speeds (for example, 2 to 20 miles per hour), turn radii 26 (for example, 30 feet to 200 feet), and straight driving acceleration/deceleration conditions 28 (for example, +0.5 g to −0.5 g). These test conditions span typically encountered levels of steering, cornering acceleration, braking acceleration, forward acceleration, and straight uniform motion produced in most day to day driving conditions on public roads and highways.

In another embodiment of the invention, the vehicle may be characterized with a computer model. For example, vehicle computer models are available from Mechanical Dynamics Corporation of Ann Arbor Mich. under the trademark ADAMS and from Mechanical Simulation Corp. under the trademark CarSim. The computer model allows a basic set of test maneuvers to be simulated for the vehicle. The basic maneuvers include city cornering, straight driving, lane changes, and acceleration/deceleration maneuvers. The maneuver simulations are run for the subject vehicle—or a similar vehicle—and the accelerations, forces, and wheel inclination angles are recorded. The use of computer models for the vehicle characterization step allows the tire manufacturer to start a wear test before a vehicle is available.

2. Course Characterization

Figure 2:
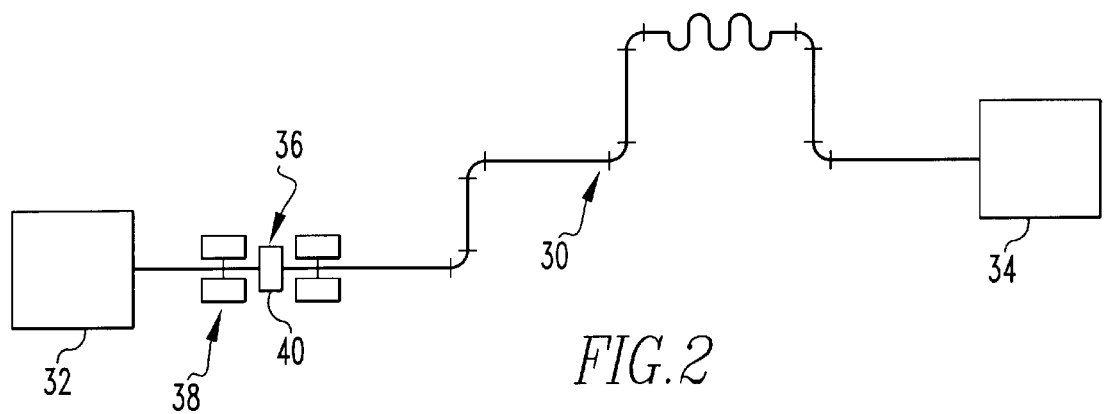
FIG. 2 is a schematic view of a wear test course being driven by a test vehicle.
Figure 3:
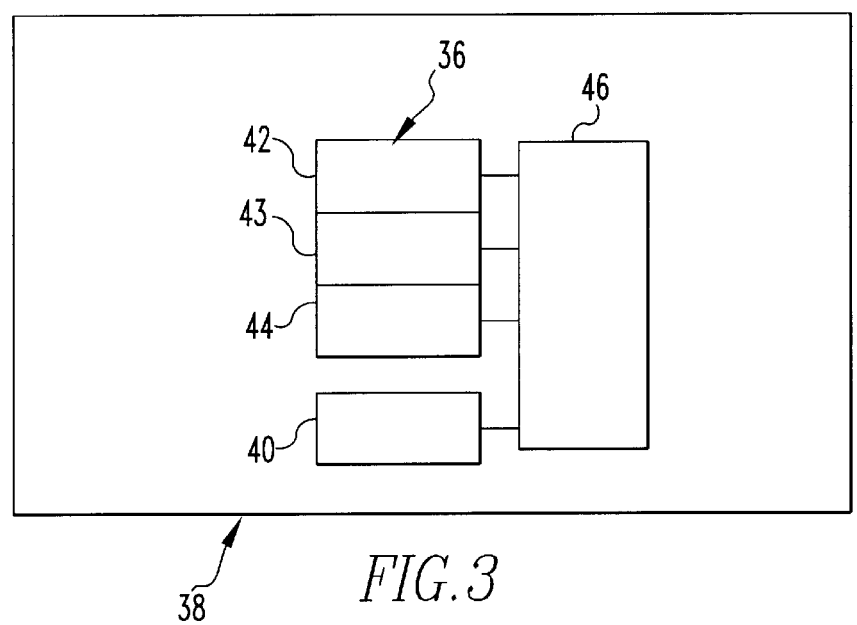
FIG. 3 is a schematic view of the instrumented vehicle depicted in FIG. 2.

Another step of the method of the present invention is to characterize a wear test course. A wear test course may be any test course of interest in which a tire manufacturer or automobile manufacturer is interested in gathering tire wear test information. For instance, the wear test course may be a typical commute for a target driver. In FIG. 2, a commuting wear course 30 includes a starting position at the driver's residence 32 and a final position at the driver's place of employment 34. The test course also may be a city driving course that would be typically used by a taxi cab driver. The wear test course may also be a route wherein the driver is given specific velocities for each part of the course. When the driver follows this type of course at the prescribed velocities, the accelerations experienced by the vehicle are relatively free of driver influence thus allowing this acceleration data to be used with a wide variety of vehicles regardless of the vehicle used to gather the data. A driver in a passenger car will not create significantly different data from the driver of a light truck because of the controlled velocities. The type of wear test courses available to the method of the present invention are essentially limitless.

Test course 30 is characterized by installing a measuring device 36 in a vehicle 38 that measures fore-aft, lateral, and vertical acceleration of the vehicle center of gravity while it is driven over course 30. An advantage is that test vehicle 38 does not have to be identical to test vehicle 14 described above. Another measurement device 40 records the velocity of the vehicle. Device 40 may be one that does not contact the road surface in order to determine velocity. Alternatively, device 40 measures the steering angle of vehicle 38 rather than the vehicle velocity. In one embodiment of the invention, three accelerometers 42, 43 and 44 are used to measure the fore-aft acceleration, the vertical acceleration, and the lateral acceleration. An appropriate data storage device 46 such as a personal computer may be in communication with measurement devices 40, 42, and 44 to record test data at regular intervals while vehicle 38 is driven over test course 30. In one embodiment, the data is recorded every one meter of travel over the entire wear test course 30. By gathering data based on distance instead of time, creating drive files is easier because the system does not gather data while the vehicle is stopped at a light or a stop sign. Gathering the data based on distance traveled is also logical because tire wear is primarily a function of distance traveled and not time. In one embodiment of the invention, a non-contacting, Doppler radar based velocity sensor (one example is available from Advanced Data Acquisition Corp.) is mounted under the vehicle close to the center of gravity. The sensor generates a signal proportional to the velocity and generates a signal that is used to pace data acquisition. This signal may be used to trigger data acquisition at a fixed distance (such as one meter) regardless of the velocity of the vehicle.

One advantage of this step over prior methods is that the instrumentation required to gather this data may be placed inside the vehicle allowing the vehicle to remain "street legal" and driven over public roads. In the past, the instrumentation was on the outside of the vehicle. The present invention also prevents inclement weather from ruining the data gathering steps. Another advantage is that devices 40, 42, and 44 are compact and may be easily shipped. The measurements devices may also be quickly installed in the test vehicle.

The data gathered over the wear test course 30 is stored and creates a mathematical test course that can be applied to different vehicles. Each cornering maneuver, each braking and acceleration event, every hill and town captured and reproduced, in real-time, in this mathematical test course. The user may drive multiple test courses in order to create a library of test courses that may be applied to vehicles as desired.

3. Model Development

After the user has characterized a vehicle, the user develops equations that relate the fore-aft force (Fx), the lateral force (Fy), the vertical force (Fz), and the inclination angle (IA) to the fore-aft acceleration (Ax), lateral acceleration (Ay), vertical acceleration (Az) and velocity (Vx) (or steering angle), measured on the wear test course. The forces, inclination angle, and velocity are needed for the indoor wear test machine. The velocity is measured during the course characterization step discussed above. Thus, the equations must relate the forces and inclination angles to the data gathered during the course characterization step described above. The equations must also be able to be used to efficiently create the drive files necessary for programming the indoor wear machines.

The equations are of the following generic functional form:

$$\{Fz, Fy, Fx, IA\} = [K]\{1, Ay, Ay^2, Ax, Ax^2, Az, C, C^2, Vx^2\}$$

where $$K = \begin{matrix} K_{11} & K_{12} & K_{13} & K_{14} & K_{15} & K_{16} & K_{17} & K_{18} & K_{19} \\ K_{21} & K_{22} & K_{23} & K_{24} & K_{25} & K_{26} & K_{27} & K_{28} & K_{29} \\ K_{31} & K_{32} & K_{33} & K_{34} & K_{35} & K_{36} & K_{37} & K_{38} & K_{39} \\ K_{41} & K_{42} & K_{43} & K_{44} & K_{45} & K_{46} & K_{47} & K_{48} & K_{49} \end{matrix}$$

Figure 4:
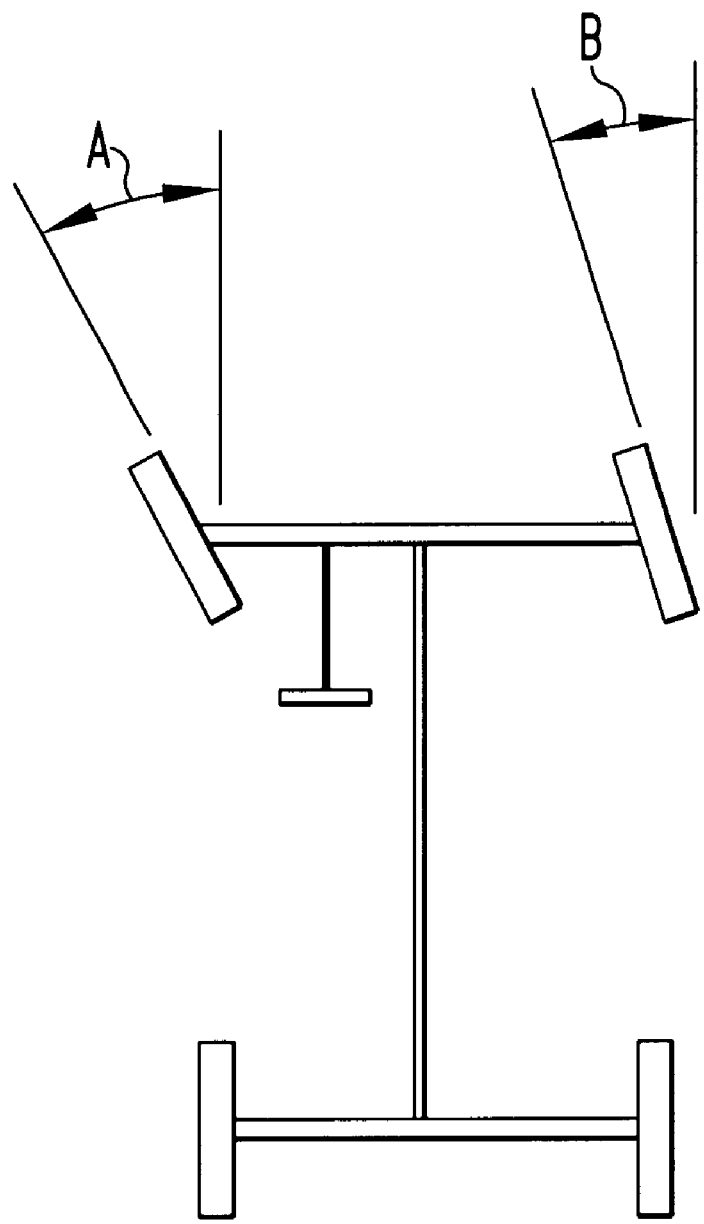
FIG. 4 is a schematic view of a vehicle showing the different steering angles of the front tires.

Fz, Fy, Fx, IA=Tire Loads and Inclination Angle
K=Vehicle Response Coefficients
1=Alignment Effects & Static Loads
$Ay, Ay^2, Ax, Ax^2, Az$=Inertial Contributions
$C, C^2$=Steering Kinematics
$Vx^2$=Aerodynamics These equations relate the forces and inclination angle to the vehicle accelerations, forward speed, and course curvature. A measure of the front position steer angle change is needed in the characterization step to account for the Ackerman effects that can significantly contribute to the lateral forces even in the absence of lateral accelerations. FIG. 4 shows why a vehicle steering system and vehicle geometry alters the angles of the tires with respect to the road surface. Angle A is different from angle B and thus the front tires experience different forces based on the radius of the curve. Road path curvature may be used to calculate these forces. However, road path curvature would have to be measured during the course characterization step. If it is not measured, the curvature may be calculated using the lateral acceleration and the velocity with the $C = A_y/V_x^2$ equation.

The coefficient matrix, K, defines the vehicle characteristics for wheel force and inclination angle dynamics. These equations are suitable for representing effects due to static loading, suspension characteristics, inertially induced load transfer, steering geometry effects, and aerodynamic contributions due to load transfer and inclination angle response. These equations have been developed for limited acceleration levels that generally do not exceed 0.5 g. This level is adequate for representing typical wear course and consumer driving conditions.

A separate set of matrix coefficients, K, are needed for each wheel position. In most situations, symmetry between left and right side wheel positions is an acceptable approximation. One method for computing the matrix coefficients uses a least squares regression to fit the modeling equations to the measured or computed-simulated data.

One additional modification is required if the indoor wear test machine (discussed in the next section) requires the spindle torque (My) as an input instead of Fx. In this case, an empirical, linear relationship between My and Fx is determined from a separate force and moment test machine for the tires under consideration and this relationship is used convert from Fx to My.

4. Indoor Mechanical Wear Test

Once the equations relating the accelerations and velocities are known, the user may program an indoor mechanical wear test machine (such as the MTS Model 860 RoadWheel Tread Wear Test System) to simulate the outdoor wear test course. The user selects a characterized wear test course and calculates the forces as they relate to time for the vehicle. These forces are input into the indoor mechanical wear test machine and a number of miles is selected for the test. The indoor mechanical wear test machine rotates the tire against the drum and creates the forces input by the user. The wear test machine continuously repeats the wear test course as if the tire was being driven over the wear test course for the selected number of miles. For instance, the user may test the tire over a commuting course for 15,000 miles.

The method of the present invention allows tires to be efficiently and accurately wear tested using indoor testing equipment. The method allows the indoor testing equipment to effectively simulate each tire position of a particular vehicle traveling on a specific outdoor road wear course. The method allows the characterized vehicles to be tested on any characterized wear test course and allows a single wear test course to be used with any characterized vehicle.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

What is claimed is:

1. A method of wear testing a tire comprising the steps of:
   (a) characterizing a vehicle using a computer model;
   (b) characterizing a wear course;
   (c) predicting force data that represents the forces that would be experienced by the characterized vehicle if the characterized vehicle were driven over the characterized wear course; and
   (d) using the force data to drive an indoor tire wear test machine.

2. The method of claim 1, wherein step (c) includes the step of relating the wear course characterization to the vehicle characterization.

3. The method of claim 2, wherein the step of relating the wear course characterization to the vehicle characterization includes the step of predicting the tire forces that would be experienced by a tire driven over the wear course by:
   (i) measuring the fore-aft, lateral, and vertical accelerations experienced by a vehicle when the vehicle is driven over the wear course;
   (ii) measuring the velocities of the vehicle when the vehicle is driven over the wear course;
   (iii) using the computer model to predict the three directional forces in response to different accelerations and velocities during different driving maneuvers; and
   (iv) creating formulas that relate the wear course accelerations and velocities to the three directional forces experienced by the tire.

4. The method of claim 3, wherein steps (i) and (ii) are performed by mounting measuring devices to a vehicle and driving the vehicle over the wear course.

5. The method of claim 4, further comprising the step of mounting the measuring devices inside the vehicle.

6. The method of claim 3, wherein the measurements of steps (i) and (ii) are taken at fixed distances along the wear course.

7. A method of wear testing a tire comprising the steps of:
   (a) driving a first vehicle over a wear test course and recording accelerations and velocities experienced by the first vehicle while the vehicle is driven over the wear test course, the accelerations and velocities being recorded at fixed distances along the wear test course;
   (b) relating tire force and inclination angle measurements to the accelerations and velocity of a second vehicle; and (c) predicting the tire forces and inclination angles that would be created in the tires of a vehicle driven over the wear test course; and (d) inputting the predicted tire forces and inclination angles into an indoor tire wear test machine.

8. The method of claim 7, wherein step (a) includes the steps of measuring the fore-aft acceleration, lateral acceleration, vertical acceleration, and velocity of the first vehicle.

9. The method of claim 8, further comprising the step of mounting the measuring devices inside the vehicle.

10. The method of claim 9, further comprising the step of driving the first vehicle over a wear teat course that includes public roads.

11. The method of claim 8, wherein step (b) includes the step of creating formulas that relate the accelerations and velocities to the three directional forces experienced by a tire.

12. The method of claim 11, wherein step (b) further includes the step of compensating at least one of the directional forces based on the turning radius of the vehicle.

13. A method of wear testing a tire comprising the steps of:

(a) selecting a first test vehicle having at least a first test tire;

(b) using a computer model to measure the forces experienced by the at least first test tire while measuring the accelerations and velocity of the vehicle;

(c) creating formulas that relate the forces experienced by the at least one test tire to the accelerations and velocity of the vehicle;

(d) driving a second test vehicle over a wear test course and recording the velocity and accelerations of the vehicle as it is driven over the wear test course, the velocity and accelerations being measured at fixed distances along the wear test course;

(e) using the velocities and accelerations recorded over the wear test course to create input forces for an indoor wear test machine;

(f) inputting the input forces into the wear test machine; and (g) performing an indoor wear test on a tire with the wear test machine using the input forces.

14. The method of claim 13, wherein step (b) includes measuring the wheel inclination angle of the at least first test tire while measuring the accelerations and velocity.

15. The method of claim 14, wherein step (c) includes the step of creating a formula that relates the wheel inclination angle to the accelerations and velocity of the vehicle.

16. The method of claim 13, wherein step (d) includes the step of measuring the fore-aft and lateral accelerations experienced by a vehicle when the vehicle is driven over the wear course.

* * * * *